United States Patent
Massen

(10) Patent No.: US 7,095,886 B2
(45) Date of Patent: Aug. 22, 2006

(54) ARRANGEMENT AND METHOD FOR PRODUCING PHOTOGRAMMETRIC IMAGE RECORDS

(75) Inventor: Robert Massen, Oehningen-Wangen (DE)

(73) Assignee: corpus.e AG, Stuttgart (DE)

( * ) Notice: Subject to any disclaimer, the term of this patent is extended or adjusted under 35 U.S.C. 154(b) by 714 days.

(21) Appl. No.: 10/398,237

(22) PCT Filed: Oct. 5, 2001

(86) PCT No.: PCT/EP01/11533

§ 371 (c)(1),
(2), (4) Date: Apr. 3, 2003

(87) PCT Pub. No.: WO02/31440

PCT Pub. Date: Apr. 18, 2002

(65) Prior Publication Data

US 2004/0032595 A1  Feb. 19, 2004

(30) Foreign Application Priority Data

Oct. 7, 2000 (DE) ................. 100 49 926

(51) Int. Cl.
*G06K 9/00* (2006.01)
*G01B 11/24* (2006.01)

(52) U.S. Cl. ...................... 382/154; 356/603

(58) Field of Classification Search ........... 382/103, 382/108, 151, 154, 203, 287, 294, 306; 345/419–420; 348/42, 47–51; 356/12, 602, 603
See application file for complete search history.

(56) References Cited

U.S. PATENT DOCUMENTS 4,294,544 A * 10/1981 Altschuler et al. .......... 356/610

(Continued)

FOREIGN PATENT DOCUMENTS

DE    3545875 A1    2/1989

(Continued)

OTHER PUBLICATIONS

Patent Abstract of Japan, JP 07-260451 A, Dated Oct. 13, 1995.

(Continued)

Primary Examiner—Daniel Miriam
(74) Attorney, Agent, or Firm—Stuart J. Friedman

(57) ABSTRACT

In the automatic photogrammetric 3D digitization of a body or body part marked e.g. by an envelope provided with photogrammetric target markers, the camera employed for image recording has additional light pattern projectors added thereon which are fastened to the camera body and project geometrically simple structures such as points or lines onto the body. These structures, which are visible optically without the viewing image, facilitate the manual alignment of the camera and the positioning of the camera at the correct distance from the body in obtaining the numerous overlapping individual images required for photogrammetric evaluation. This manually predefined alignment facilitates the automatic association of the photogrammetric markers in the individual image pairs with the aid of image processing methods and allows it to be carried out more reliably on an automated basis. According to a preferred embodiment, the projectors are turned off in the actual image recording process.

30 Claims, 2 Drawing Sheets

U.S. PATENT DOCUMENTS

| | | | |
|---|---|---|---|
| 4,431,290 A | 2/1984 | Kennedy | |
| 4,819,660 A | 4/1989 | Smith | |
| 4,846,577 A * | 7/1989 | Grindon | 356/610 |
| 5,911,126 A * | 6/1999 | Massen | 702/153 |
| 6,363,169 B1 * | 3/2002 | Ritter et al. | 382/154 |
| 6,549,289 B1 * | 4/2003 | Ellis | 356/603 |
| 6,724,930 B1 * | 4/2004 | Kosaka et al. | 382/154 |
| 6,930,704 B1 * | 8/2005 | Hamada | 348/42 |
| 6,993,179 B1 * | 1/2006 | Weinshall et al. | 382/154 |

FOREIGN PATENT DOCUMENTS

| | | |
|---|---|---|
| DE | 3632450 A1 | 7/1989 |
| DE | 4115445 C2 | 1/1992 |
| DE | 4130237 A1 | 4/1994 |
| DE | 4313104 A1 | 10/1994 |
| DE | 44 33 197 | 8/1995 |
| DE | 19536297 A1 | 4/1997 |
| DE | 19637682 A1 | 3/1998 |
| DE | 19714383 A1 | 9/1998 |
| DE | 19852149 A1 | 5/2000 |
| DE | 10025922 | 12/2001 |
| EP | 0226732 | 2/1989 |
| EP | 0 760 622 | 3/1997 |

OTHER PUBLICATIONS

German Search Report (Dated Aug. 27, 2001).

* cited by examiner

ARRANGEMENT AND METHOD FOR PRODUCING PHOTOGRAMMETRIC IMAGE RECORDS

FIELD OF THE INVENTION

The invention relates to an arrangement and a method for obtaining image recordings from which the 3D shape of an object can be determined by photogrammetry.

BACKGROUND OF THE INVENTION

Numerous products need to be adapted to the individual shape of the object for which they are intended, such as e.g. a body part. For instance, many products that are in contact with the human body, such as footwear, shirts, pants, gloves, orthopedic articles such as elastic stockings and bandages, sport supports, spectacle frames, etc., need to fit well, i.e. their three-dimensional geometry must correspond to the three-dimensional shape in space of the respective part of the body. These fitting requirements do not only apply to products which need to be adapted to the human body but, in a broader sense, also to products or components which need to be adapted to technical bodies. To mention an example, a plastic casing is to be adapted to the mechanical base frame of a household appliance.

The sensing of the 3D shape, i.e. the three-dimensional geometry, of bodies is nowadays done by means of so-called 3D scanners, for example, which usually operate using methods based on stripe projection, laser triangulation, stereo measurement, photogrammetry, and the methods of point-by-point scanning of the distance of the object of the body to be sensed using a distance measuring device. Where these devices serve to measure the human body, they are often referred to as "body scanners", while they are called "3D digitizers" for more technical applications. In all of these methods, relatively complex and, hence, expensive electrooptical systems are employed. For instance, currently used body scanners cost between £100,000 and £250,000.

In European Patent EP 0 760 622, "Digitized Sensing Process and Arrangement for the Three-Dimensional Shape in Space of Bodies or Body Parts", the inventor, R. Massen, describes an extremely low-cost way of sensing the 3D shape of body parts which is based on multiple camera or single camera photogrammetry. In this process, the body part to be digitized is covered with a tight-fitting elastic envelope which is provided with target markers adapted to be evaluated photogrammetrically. The body part is imaged from different spatial positions which need not necessarily be known or fixed in space, and the space coordinates of the target markers are determined from the overlapping individual images with the aid of photogrammetric methods of reconstruction, which allows to determine the three-dimensional shape of the body.

In German Patent Application 100 25 922.7, the inventor, R. Massen, describes various methods of how an automatic registration, i.e. an association of the punctiform target markers in image pairs, can be carried out more easily by way of encoding the background between punctiform target markers in the form of area markers. For instance, it is described how corresponding regions in two images can be determined in a simple manner using the methods of digital color image processing, by a colored marking over an area of background regions of the punctiform target markers based on a simple color classification.

For a photogrammetric reconstruction of an object to be possible, it is necessary that pairs of image recordings overlap to a sufficient extent, i.e. that as many identical target markers as possible are contained in two corresponding image recordings which have an at least partially overlapping image area.

The 3D coordinates of the target markers can be calculated the more easily and accurately the better the camera positions that were assumed by the camera while recordings of a pair of images with overlapping image areas were obtained are aligned in relation to each other. Since, as a rule, the inner parameters of the camera such as the focal length, the number and size of the pixels (in the case of a digital camera), the position of the optical axis in relation to the focal plane, etc., were determined by a previous calibration and need to be constant throughout the recordings, the focal length needs to be kept constant. This means that no zoom functions may be used and that autofocus means must also be switched off. Accordingly, sharply focused images can only be attained if the distance of the camera to the body part to be scanned is approximately constant in all positions in space.

This condition is only very difficult to fulfill for an operator who leads the camera free-handed around the body part to be sensed while obtaining the image recordings to be evaluated photogrammetrically, which makes it considerably more difficult, especially for a layman, to obtain the image recordings in a simple manner.

The background markings that combine a plurality of punctiform target markers to form an area as described in German Patent Application 100 25 922.7 are already very useful to the automatic photogrammetric evaluation of the image recordings of the body part marked by e.g. a tight-fitting envelope. However, the demands made on the image processing methods are still high if the corresponding target markers from image pairs have to be found, where nothing is known about the orientation of the camera in space while the recordings are obtained. Search procedures are then required which are involved and, hence, prone to error, in order to prevent that target markers in the respectively analyzed pair of image recordings are associated with each other which in fact do not correspond.

SUMMARY OF THE INVENTION

It is therefore the object of the present invention to provide an arrangement for and a method of obtaining image recordings from which the 3D shape of an object can be determined by photogrammetry, which allow a simple preparation—easy to be carried out even by laymen or inexperienced users—of image recordings overlapping in the image area which are suitable for an accurate, simple and reliable automatic photogrammetric evaluation.

The object of the invention is achieved by an arrangement for obtaining image recordings from which the 3D shape of an object can be determined by photogrammetry, comprising at least one image recording system and a plurality of target markers applied on the surface of the object and adapted to be evaluated photogrammetrically, which is characterized in that the arrangement further includes a means for generating projected light markings which is mounted to the image recording system or systems and alignment markers on the surface of the object each of which can be associated with an individual one of the image recordings to be obtained for the photogrammetric sensing, the means for generating projected light markings and the alignment markers respectively associated with the image recordings being positioned in relation to each other such that when the image recording system or systems, prior to recording each image, is/are positioned in relation to the object such that light markings generated by the means for generating projected light markings are projected onto the surface of the object in a predetermined position in relation to the alignment markers intended for the respective image recording, the image recordings are obtained in a manner so as to allow a photogrammetric evaluation of the image recordings using the target markers and, from this, the determination of the 3D shape of the object.

The object of the invention is further achieved by a method of obtaining image recordings from which the 3D shape of an object can be determined by photogrammetry, wherein target markers adapted to be evaluated photogrammetrically are applied onto the surface of the object and alignment markers are provided each of which is associated with an individual one of the image recordings to be obtained for the photogrammetric sensing, at least one image recording system is provided which has mounted thereto a means for generating projected light markings, the image recording system or systems, prior to recording each image, is/are positioned in relation to the object such that light markings generated by the means for generating projected light markings are projected onto the surface of the object in a predetermined position in relation to the alignment markers provided for the respective recording, and the recordings are obtained using the image recording system or systems.

The invention permits to achieve image recordings in a simple manner, which may be very accurately evaluated photogrammetrically. In accordance with the invention, this is achieved in that the image recording system provided for photogrammetric sensing of an object has optical aids mounted thereto which are able to generate light markings on the object which are aligned by a user to form alignment markers prior to obtaining an image, the alignment markers being applied on the object, so that the alignment and the distance between the object and the image recording system can be maintained in the various recordings as desired. This permits the use of very simple and inexpensive image recording systems for obtaining the recordings, such as web cameras without a viewfinder.

Advantageous further developments of the invention are identified in the dependent claims.

Further features and advantages of the invention will be apparent from the following description of an embodiment with reference to the drawings, in which:

The arrangement and the method according to the invention will now be described by way of example with reference to a case of application in the field of orthopedics, namely, the 3D digitization of legs for an automated adaptation of elastic stockings. Of course, many other applications are conceivable and the example described is therefore not to be construed in a limiting sense.

Figure 1:
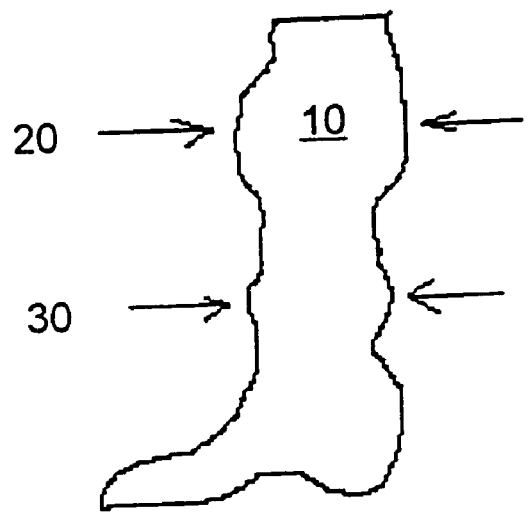
FIG. 1 shows a leg with diseased veins as an example of an object to be sensed photogrammetrically, which can be imaged by means of the arrangement according to the invention.

FIG. 1 schematically illustrates a leg 10 with diseased veins, whose 3D shape is to be sensed photogrammetrically from the foot up and approximately as far as to the crotch, in order that an elastic stocking adapted to the leg can be manufactured such that a greater pressure can be exerted on the tissue at the places showing the pathologic swellings 20 and 30 than at the sound places.

Figure 2:
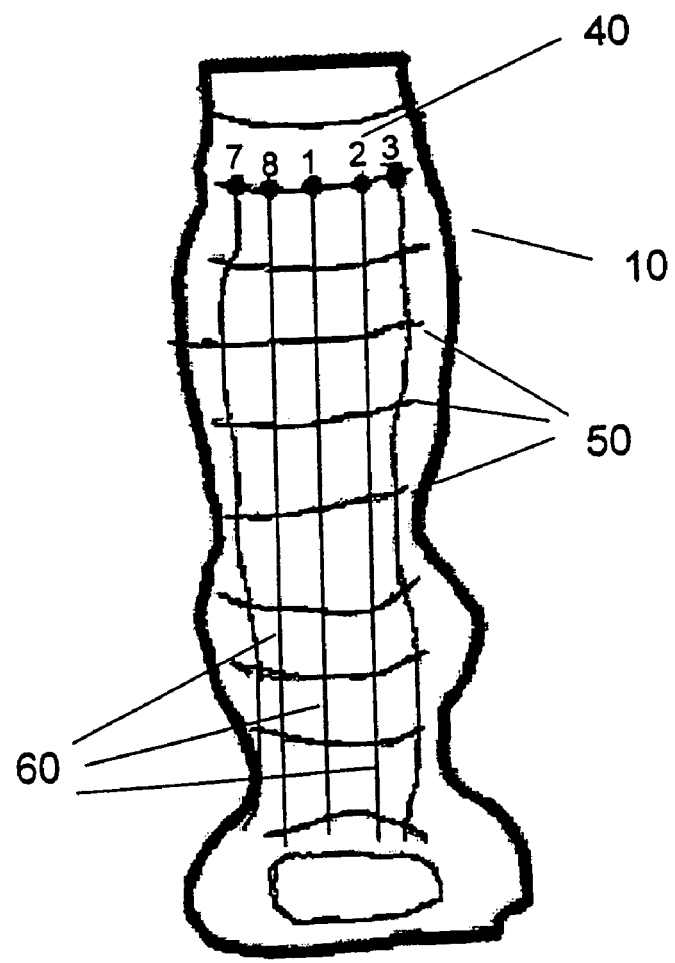
FIG. 2 shows the leg of FIG. 1, marked with target markers and alignment markers used in accordance with the invention.

FIG. 2 shows the leg 10 as covered with a marked tight-fitting envelope 40 in accordance with European Patent EP 0 760 622 mentioned at the outset, the target markers adapted to be evaluated photogrammetrically being defined by vertical 50 and horizontal 60 dark lines applied on the envelope, the points of intersection of the lines 50 and 60 forming the punctiform target markers adapted to be evaluated photogrammetrically. In addition, by way of example eight markers are applied on the envelope which are identified by the numbers 1, 2, 3, . . . , 8. For reasons of perspective, of these further eight markers only the markers identified by the numbers 1, 2, 3, 7 and 8 are visible in FIG. 2, the remaining markers being applied on the other side of the envelope. The markers 1, 2, . . . 8 serve as alignment markers for the image recording system which is to be used for obtaining the photogrammetric recordings, with each of the punctiform alignment markers corresponding to a recording position for the images to be obtained all around the leg. The alignment markers are numbered consecutively to assist the operator of the image recording system, in the present example a digital color camera, with the numbers 1, 2, . . . 7, 8 shown in FIG. 2 serving both as reference numbers and as numbering and thus as an indication of the order in which the points have to be addressed by the image recording system.

In the present example, the camera is intended to be guided by the operator free-handed all around the leg 10 in eight overlapping spatial positions while the image recordings to be evaluated photogrammetrically are obtained.

With no aid available, it is extraordinarily difficult for the user to guide a camera which, as described in the introductory part of the specification, has a fixed focal length and therefore no autofocus options, at a constant distance from the surface of the leg and to align the camera such that the automatic association of the images on the basis of the target markers (in this case the points of intersection between the lines 50 and 60) is possible in a simple way. In addition, it is very difficult to attain the precise alignment and the correct distance merely by viewing through the viewfinder or by an observation of the LCD viewfinder screen, if provided, because the operator of the camera needs to concentrate on the patient.

Figure 3:
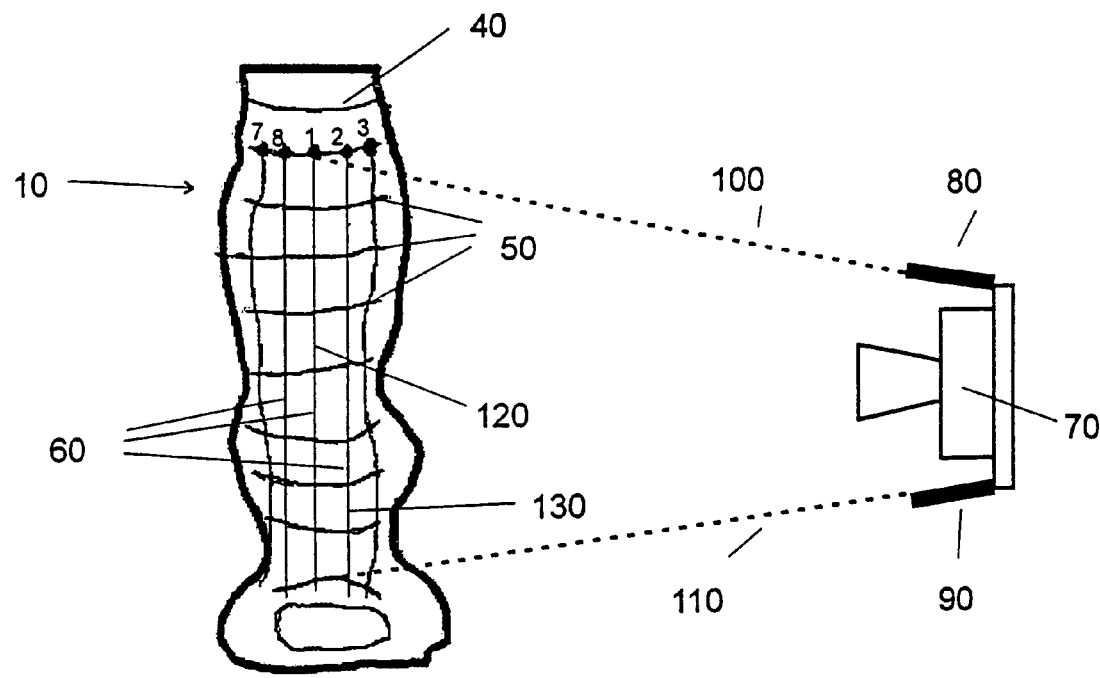
FIG. 3 shows one embodiment of an arrangement according to the invention for obtaining image recordings from which the 3D shape of an object can be determined by photogrammetry, in a view from the side.

In accordance with the invention and as shown in FIG. 3, the camera 70 is equipped with a pair of spotlight projectors 80 and 90 which are firmly secured to the camera and may consist, e.g., of a pair of laser diode spot projectors. As can be seen in FIG. 2, the spotlight projectors are arranged at an angle to each other such that the light beams 100 and 110 generated by the spotlight projectors diverge the more the greater the distance from the camera, i.e. that the distance between the two light beams 100 and 110 increasingly grows as the distance of the light beams from the camera increases. In this way, the two light beams 100 and 110 mark the image frame covered by the camera 70 in one dimension when impinging on the marked envelope 40.

The user may now align the camera 70 immediately with the aid of the alignment markers 1, 2, 3, . . . , 8 in such a way that the respectively captured image frame is in a known position and, hence, in a position suitable for an easy automated photogrammetric evaluation. In the present example, instructions for obtaining the first image recording would read as follows:

"First, align the camera 70 such that the laser spot generated by the upper spotlight projector 80 impinges on the alignment marker 1 applied on the envelope 40 and, in addition, align the camera 70 at the same time such that the laser spot generated by the lower spotlight projector 90 impinges on the vertical line 120 running through the alignment marker 1. With this alignment, obtain the first recording by actuating the shutter release."

This alignment of the camera 70 is illustrated in FIG. 3.

The instructions for obtaining the second image recording would then read as follows:

"First, align the camera 70 such that the laser spot generated by the upper spotlight projector 80 impinges on the alignment marker 2 applied on the envelope and, in addition, align the camera 70 at the same time such that the laser spot generated by the lower spotlight projector 90 impinges on the vertical line 130 running through the alignment marker 2. With this alignment, obtain the second recording by actuating the shutter release."

The instructions for obtaining the image recordings three through eight read correspondingly.

When the images are recorded in these imaging positions Nos. 1 to 8, which are easy to assume owing to the optical assistance by the spotlight projectors, a set of images is produced in which the orientation of the camera 70 is always the same and parallel to the vertical marking lines 60. This means that later in the photogrammetric evaluation an automated association of the target markers from the individual image recordings following a known systematics (e.g., in ascending order of the marked points) will be easy to achieve, and the target markers corresponding to each other (here: intersection points) may be easily determined using methods of 2D image processing and pattern recognition.

This method in accordance with the invention facilitates the orientation (rotary position and translation) of the camera in relation to the body part to be digitized while obtaining the image recordings, but does not facilitate the maintenance of a predetermined distance D of the camera 70 with respect to the body part.

Figure 4:
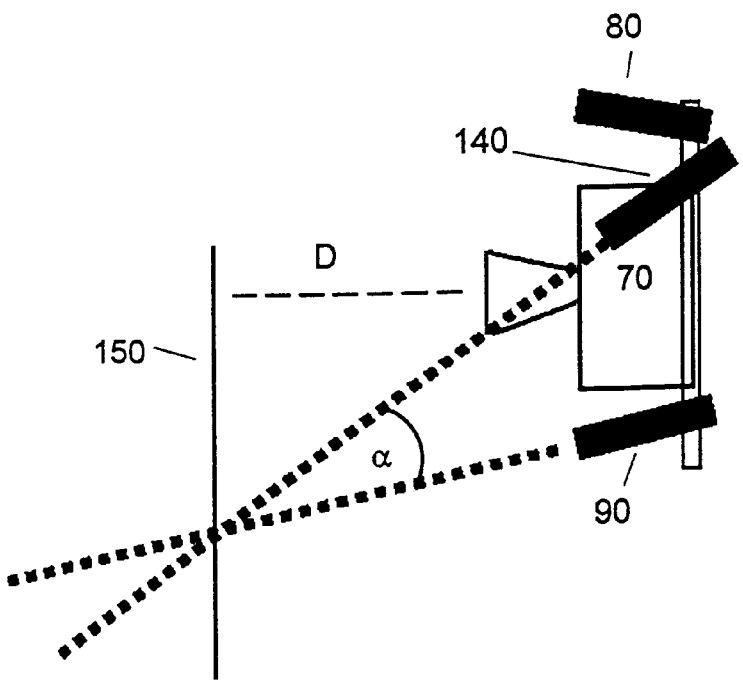
FIG. 4 shows a further embodiment of an arrangement according to the invention for obtaining image recordings from which the 3D shape of an object can be determined by photogrammetry, in a view from the side.

Therefore, in accordance with the invention, in the further embodiment of the arrangement according to the invention illustrated in FIG. 4, a further spotlight projector 140 is firmly attached to the camera 70 such that it radiates at a fixed angle α to one of the two other spotlight projectors, for instance to the projector 90. The angle α is so selected that when the predefined distance D is reached, the light spot generated by the projector 90 will be coincident with the light spot generated by the projector 140. This provides a very simple visual aid for the operator of the camera 70 in setting the right distance D between the camera 70 and the edge 150 of the object 10 to be imaged.

When the distance between the edge 150 of the object to be imaged and the camera 70 is greater or smaller than D, two light spots, spatially separated from each other, will be visible on the surface of the object, for the operator to easily recognize that the positioning of the camera requires correction.

Accordingly, for this embodiment the rule for obtaining the first image reads as follows:

"First, align the camera 70 such that the laser spot generated by the upper spotlight projector 80 impinges on the alignment marker 1 applied on the envelope 40 and, in addition, align the camera 70 at the same time such that the laser spot generated by the lower spotlight projector 90 impinges on the vertical line 120 running through the alignment marker 1, and select the distance between the camera and the body part 10 to be such that the laser spot generated by the middle spotlight projector 140 is coincident with the laser spot generated by the lower spotlight projector 90. With this alignment, obtain the first recording by actuating the shutter release."

The remaining recordings are then obtained correspondingly.

In accordance with the invention, the above-described processes of positioning the camera (using, e.g., three projected points) may also be defined using many other structures that are simple to project. For example, instead of the two light spots illustrated in FIG. 3, one continuous line may be projected onto the body or the envelope. Also, rather than using a pair of converging light beams from a pair of spotlight projectors, the adjustment of the distance may be visualized by the projection of a circle, the diameter of the circle being so selected, for example, that on reaching the correct distance the visible circle will shrink to turn into a point.

The idea of the invention further encompasses any structures adapted to be projected which visually permit an alignment of the camera with the body part or with the markings on the envelope covering the body part, without having to observe the viewing image of the camera or the electronic image produced by the camera for the purpose of alignment, as well as any structures adapted to be projected which visually allow to assume the correct distance from the body part.

The structures projected on may also be multicolored and may furthermore be configured such that when the correct distance between the camera and the object is reached, a superposition of the structures will result in a visible change of color produced at the place of superposition, serving as an indication of the correct position of the camera.

The optical aid in the form of a projection means may also be fitted to a video camera in order to produce image sequences, with the video camera running, which are recorded at the correct distance, are simply oriented with respect to each other and can be evaluated photogrammetrically in a simple manner.

In a further embodiment, the projectors may be turned off prior to recording the images, in order to prevent that the projected structures interfere with the photogrammetric target markers while the images are recorded.

In a further embodiment of the invention, the alignment markers may also be projected in a color that is easily seen by the eye as a contrast to the background. These colors can be removed again automatically from the recorded images using methods of color image processing, so that the projectors need not be turned off during the actual image recording.

In a further embodiment, the projectors will also remain turned on while recording the images and the projected structures are evaluated by means of image processing methods in order to derive information from the recorded images as to whether the recordings were obtained in the correct manner at all, that is, whether, e.g., the projected structures were located on the alignment markers. In this way, the evaluation of the structure responsive to the distance may, for instance, yield information on whether the image was recorded at the right distance.

The projected structures for verification of a correct distance or a correct orientation may also be put to use in conventional cameras employed in fields other than photogrammetry, to help the user keep a correct distance from an object to be imaged or reach a correct alignment of the camera in relation to the object.

In a further embodiment the light pattern projectors may be mechanically fastened to a solid rail and secured to the camera body via a threaded joint for the tripod, at the place where a tripod is normally fastened.

In a further embodiment of the invention, the alignment markers need not be specially applied on the object or on an envelope; instead, they may consist in natural distinct points of the object (e.g., blood vessels that are visible on a leg).

The target and alignment markers further need not necessarily be applied on an envelope; rather, they may also be projected onto the object by means of, e.g., a further projection system or be applied directly onto the object (e.g., painted on).

The means for generating projected light markings need not necessarily be lasers, but they may also be comprised of other luminiferous elements and may include LEDs, for instance.

The object to be digitized need not absolutely be a part of the human body, but may be any desired object the 3D shape of which is to be determined.

The invention finally also provides an arrangement for sensing of the 3D shape of an object by photogrammetry, comprising an arrangement in accordance with the invention for obtaining image recordings and a conventional system for measuring and evaluating the image recordings and for determining the 3D shape of the object.

What is claimed is:

1. An arrangement for obtaining image recordings from which the 3D shape of an object can be determined by photogrammetry, comprising at least one image recording system (70) and a plurality of target markers (50, 60) applied on the surface of the object (10) and arranged to be evaluated photogrammetrically, the arrangement including a means (80, 90, 140) for generating projected light markings which as mounted to the image recording system or systems (70) and alignment markers (1, 2, 3, . . . , 8) on the surface of the object (10) each of which can be associated with an individual one of the image recordings to be obtained for the photogrammetric sensing, the means (80, 90, 140) for generating projected light markings and the alignment markers (1, 2, 3, . . . , 8) respectively associated with the image recordings being positioned in relation to each other such that when the image recording system or systems (70), prior so recording each image, is/are positioned in relation to the object (10) such that light markings generated by the means for generating projected light markings are projected onto the surface of the object (10) in a predetermined position in relation to the alignment markers (1, 2, 3, . . . , 8) provided for the respective image recording, the image recordings are obtained in a manner so as to allow a photogrammetric evaluation of the image recordings using the target markers (50, 60) from which evaluation can be determined 3D shape of the object (10).

2. The arrangement according to claim 1, wherein the means for generating projected light markings and the alignment markers respectively associated with the image recordings are positioned in relation to each other such that when the image recording system or systems, prior to recording each image, is/are positioned in relation to the object such that light markings generated by the means for generating projected light markings are projected onto the surface of the object in a predetermined position in relation to, the alignment markers intended for the respective image recording, the alignment between the image recording system or systems and the object remains constant while each image is recorded.

3. The arrangement according to claim 2, wherein the means for generating projected light markings are arranged at an angle to each other and the alignment markers consist of a point and a straight line connected with this point.

4. The arrangement according to claim 2, wherein the means for generating projected light markings consist of a pair of light projectors (80, 90) arranged at an angle to each other such that the light beams generated by them diverge and the alignment markers for one image recording each consist of a point and a straight line connected with this point.

5. The arrangement according to claim 1, wherein the means for generating projected light markings and the alignment markers respectively associated with the image recordings are positioned in relation to each other such that when the image recording system or systems, prior to recording each image, is/are positioned in relation to the object such that light markings generated by the means for generating projected light markings are projected onto the surface of the object in a predetermined position in relation to the alignment markers intended for the respective image recording, the distance between the image recording system or systems and the object remains constant while each image is recorded.

6. The arrangement according to claim 5, wherein the means for generating projected light markings consist of a pair of light projectors (90, 140) arranged at an angle to each other such that the light beams generated by them converge and the alignment markers for one image recording each consist of a point.

7. The arrangement according to claims 2 or 5, wherein the means for generating projected light markings and the alignment markers respectively associated with the image recordings are positioned in relation to each other such that when the image recording system or systems prior to recording each image, is/are positioned in relation to the object such that light markings generated by the means for generating projected light markings are projected onto the surface of the object in a predetermined position in relation to the alignment markers provided for the respective image recording, the distance and the alignment between the image recording system or systems and the object remain constant while each image is recorded.

8. The arrangement according claim 7, wherein the means for generating projected light markings consist of three light projectors, two of which (80, 90) are arranged at an angle such that the light beams generated by them diverge, the third light projector (140) being at an angle to as least one of the two light projectors such that the light beams generated by the third light projector and the one of the two light projectors converge and the alignment markers for one image recording each consist of a point and a straight line connected with this point.

9. The arrangement according to claim 1, wherein the projected light markings are punctiform.

10. The arrangement according to claim 9, wherein the means for generating projected light markings are arranged at an angle to each other and the alignment markers consist of a point and a straight line connected with this point.

11. The arrangement according to claim 9, wherein the means for generating projected light markings consist of a pair of light projectors (80, 90) arranged at an angle to each other such that the light beams generated by them diverge and the alignment markers for one image recording each consist of a point and a straight line connected with this point.

12. The arrangement according to claim 9, wherein the means for generating projected light markings consist of a pair of light projectors (90, 140) arranged at an angle to each other such that the light beams generated by them converge and the alignment markers for one image recording each consist of a point.

13. The arrangement according to claim 9, wherein the means for generating projected light markings consist of three light projectors, two of which (80, 90) are arranged at an angle such that the light beams generated by them diverge, the third light projector (140) being at an angle to at least one of the two light projectors such that the light beams generated by the third light projector and the one of the two light projectors converge and the alignment markers for one image recording each consist of a point and a straight line connected with this point.

14. The arrangement according to claim 1, wherein the projected light markings are in the shape of a line.

15. The arrangement according to claim 1, wherein the alignment markers are numbered consecutively in accordance with the order of the image recordings to be obtained.

16. The arrangement according to claim 1, wherein the alignment markers consist of distinct points of the object.

17. The arrangement according to claim 1, further including an elastic envelope which has the target markers and the alignment markers applied thereon and is designed so as to be pulled over the object and to adapt to the shape of the object.

18. The arrangement according to claim 1, further comprising a projection system which is designed to be used for projecting the target markers and the alignment markers onto the object.

19. The arrangement according to claim 1, wherein the image recording system is comprised of a digital camera without a viewfinder, which can be panned free-handed around the object while the images are recorded.

20. The arrangement according to claim 1, wherein the means for generating projected light markings are lasers.

21. The arrangement according to claim 1, wherein the means for generating projected light markings are LEDs.

22. The arrangement according to claim 1, wherein the object is a part of human body.

23. An arrangement for photogrammetric sensing of the 3D shape of an object, comprising an arrangement for obtaining image recordings according to claim 1 and a system for measuring and evaluating the recorded images and for determining the 3D shape of the object.

24. A method of obtaining image recordings from which the 3D shape of an object can be determined by photogrammetry, wherein target markers arranged to be evaluated photogrammetrically are applied onto the surface of the object and alignment markers are provided, each of which is associated with an individual one of the image recordings to be obtained for the photogrammetric sensing, at least one image recording system is provided which has mounted thereto a means for generating projected light markings, the image recording system or systems, prior to recording each image, is/are positioned an relation to the object such that light markings generated by the means for generating projected light markings are projected onto the surface of the object in a predetermined position in relation to the alignment markers provided for the respective recording, from which the 3D shape of the object can be determined.

25. The method according to claim 24, wherein the means for generating projected light markings is turned off while the image recordings are obtained so as to prevent the light markings from appearing on the recorded images.

26. The method according to claims 24 or 25, wherein the target markers are also applied onto the object.

27. The method according to claim 26, wherein the application of the target and alignment markers is effected in such a way that an elastic envelope which has the target and alignment markers applied thereon as pulled over the object.

28. The method according to claim 26, wherein the application of the target and alignment markers is effected in such a way that they are projected on the surface of the object.

29. The method according to claim 24, wherein the image recording system is comprised of a digital camera without a viewfinder, which is guided free-handed around the object.

30. A method of sensing the 3D shape of an object by photogrammetry, wherein a plurality of image recordings are obtained in accordance with the method of claim 24, an image processing is performed in which the target markers respectively corresponding in the image recordings are associated with each other and then, using the target marker association, the 3D shape of the object is determined by means of a photogrammetric evaluation process.

* * * * *